US011503965B2

(12) United States Patent
Venturino

(10) Patent No.: US 11,503,965 B2
(45) Date of Patent: Nov. 22, 2022

(54) MULTI-PURPOSE CONTAINER FOR THE PROVISION OF CLOTHS HAVING AN AIR FRESHENING FUNCTION

(71) Applicant: Cupssy GmbH, Schöneck (DE)

(72) Inventor: Enzo Venturino, Schöneck (DE)

(73) Assignee: Cupssy GmbH, Schöneck (DE)

( * ) Notice: Subject to any disclaimer, the term of this patent is extended or adjusted under 35 U.S.C. 154(b) by 70 days.

(21) Appl. No.: 16/878,698

(22) Filed: May 20, 2020

(65) Prior Publication Data

US 2021/0000307 A1    Jan. 7, 2021

(30) Foreign Application Priority Data

May 22, 2019  (DE) ................. 10 2019 113 672.5

(51) Int. Cl.
*A47K 10/32*        (2006.01)

(52) U.S. Cl.
CPC ........ *A47K 10/32* (2013.01); *A47K 2010/322* (2013.01); *A47K 2010/3233* (2013.01)

(58) Field of Classification Search
CPC ..................................... A47K 10/32
USPC ..................................... 221/33–63
See application file for complete search history.

(56) References Cited

U.S. PATENT DOCUMENTS

| 6,158,614 | A | 12/2000 | Haines et al. |
| 2011/0060457 | A1* | 3/2011 | De Vrught ........... A61J 1/03 700/241 |
| 2014/0103059 | A1* | 4/2014 | Mothaffar ........... A47K 10/42 221/34 |
| 2015/0374182 | A1* | 12/2015 | Delaney ........... A47K 10/38 221/1 |

FOREIGN PATENT DOCUMENTS

| DE | 10 2018 003 669 | 1/2019 |
| JP | 11-049257 | 2/1999 |

* cited by examiner

*Primary Examiner* — Gene O Crawford
*Assistant Examiner* — Ayodeji T Ojofeitimi
(74) *Attorney, Agent, or Firm* — Clark & Brody LP

(57) ABSTRACT

The invention relates to a multi-purpose container (1) with an air freshening function for receiving cloths (31), in particular for use in a drink holder of a vehicle. The multi-purpose container comprises a housing (10) with a lid (20) for forming a receiving space (13) in the housing (10). The lid (20) has an opening (22) for the removal of cloths (31) from the receiving space (13) and a receiving recess (21) for receiving the scented insert (40).

13 Claims, 5 Drawing Sheets

MULTI-PURPOSE CONTAINER FOR THE PROVISION OF CLOTHS HAVING AN AIR FRESHENING FUNCTION

FIELD OF THE INVENTION

The invention relates to a multi-purpose container with an air freshening function and for the provision of cloths, in particular for use in a drink holder of a vehicle. Furthermore, the invention relates to a scented insert and also to a cartridge.

BACKGROUND ART

Summary of the Invention

A multiplicity of vehicles are currently equipped with drink holders or cup holders. By way of example, drink holders of this kind can be arranged in a centre console, on a glove compartment or in the region of rear seats of the vehicle. In particular, drink holders arranged in the centre console are usually of doubled embodiment.

DE 10 2005 028 586 A1 for example describes a drink holder for receiving cups or drink bottles. The drink holder is integrated in a centre console of the vehicle and has two places for receiving cups or bottles. Often, only one receiving place, for example for the deposition of drink bottles, is used. The second receiving place frequently remains unused in the case of drink holders of this kind.

The invention is then based on the object of proposing a multi-purpose container which equips unused receiving places of drink holders with additional functions.

The invention relates to a multi-purpose container with an air freshening function for the provision of cloths, in particular for use in a drink holder of a vehicle. The multi-purpose container has a housing and a lid for closing the housing and for forming a receiving space in the housing. Furthermore, the multi-purpose container has a scented insert. According to the invention, the lid has an opening for the removal of cloths from the receiving space, wherein a receiving recess for receiving the scented insert is provided in the lid.

The multi-purpose container can preferably be designed as a cup which can be closed by the lid and which can be inserted into a receiving place of a drink holder. To this end, the housing can have a substantially cylindrical form, which is flared in the direction of the lid. In this way, the multi-purpose container can also be usable with foldable and also bottomless drink holders.

Furthermore, the multi-purpose container can have a bottom-side adapter sleeve, by way of which the multi-purpose container can be adjusted to drink holders with larger diameters. The adapter sleeve can be embodied in the form of a cover made of an elastic material, such as, for example, silicone or elastomer.

The lid attached to the housing delimits an internal volume of the housing and thus forms a receiving space. The receiving space is preferably used for receiving cloths. The cloths can be individually removed via the opening which is introduced into the lid.

In an advantageous configuration, after a cloth has been removed, a projecting portion of a subsequent cloth remains in the opening of the lid, such that removal of cloths from the receiving space is simplified.

The cloths can for example be designed as paper tissues, cleaning cloths, wipes, glass cleaning cloths for window panes or spectacles, leather care cloths, cloths for cleaning plastics, disinfection cloths, refreshing cloths, cloths for inspecting the engine oil level, perfumed cloths and the like. Various areas of application of the multi-purpose container are thus possible in dependence on the impregnation and type of the cloths.

In addition, it is possible to change the area of application of the multi-purpose container by acquiring and inserting different cloth refill packs.

As a result of the use of a scented insert, it is possible to expand the scope of function of the multi-purpose container by an air freshening function. The scented insert can preferably be available in various scent types and can be inserted into the receiving recess of the lid. Preferably, the scented insert can be embodied as a scented cushion or a scented pad, which can be attached next to the opening of the lid. The scented insert can react chemically with air in order to release aromatic substances. Preferably, the scented insert can be formed in a ring-shaped manner and can be positionable concentrically with respect to the opening. Furthermore, the cloths in the receiving space thus remain accessible through the opening of the lid.

Use of the multi-purpose container according to the invention makes it possible for consumers to equip the unused drink holders or receiving places of drink holders of a vehicle with one or more add-ons, which are tailored to their needs and desires, in the form of multi-purpose containers, and to use these containers in a cost-effective manner over a long period of time by purchasing scented inserts and cloths.

According to one embodiment, the receiving space of the housing is configured to receive cloths, wherein the cloths can be inserted in a cartridge or directly in the receiving space. The cloths can be positionable, directly and without additional means, in the housing. Preferably, the cloths can be pre-folded or formed to match a form of the receiving space.

As an alternative, the cloths can be arranged in a cartridge, wherein the cartridge can be inserted into the receiving space in a positively locking manner. As a result of the use of a cartridge with cloths, refilling of the multi-purpose container with new cloths can be simplified and accelerated. The cartridge can preferably have a form which corresponds to the receiving space. In particular, the cartridge can have a cylindrical form.

The handling of the scented insert can be simplified if the scented insert can be inserted into a receiving unit, wherein the receiving unit, with the scented insert inserted, can be placed in the receiving recess of the lid. By way of example, the receiving unit can be embodied as a constituent part of a packaging of the scented insert, wherein the scented insert can be packaged between the receiving unit and a removable packaging lid. The scented insert can be inserted with the packaging into the receiving recess, and the packaging lid can subsequently be removed. As an alternative, the receiving unit can be composed of an elastic material and can be provided for the positively locking storage of the scented insert.

The receiving unit is preferably designed in such a way that the scented insert protrudes about 50% in a thickness direction. The other half of the scented insert is thus covered by the receiving unit. As a result, a long useful life of the scented insert is achieved, since only the protruding region releases aromatic substances, whereas the region covered by the receiving unit does not react. By rotating the scented insert, it is thus possible to double the useful life.

According to a further embodiment, the multi-purpose container has a metering unit which conceals the scented insert at least in certain regions. The metering unit can preferably be designed to be displaceable or rotatable relative to the scented insert. The metering unit can for example rest on one side of the scented insert and cover a defined area of the scented insert. In this way, a chemical reaction of the scented insert is prevented in the region of the covered area. As a result of a displacement or rotation of the metering unit, the covered area can be made accessible when a chemical reaction with air and thus a release of scent is desired. The metering unit thus makes it possible to regulate or adjust the intensity of the air freshening on the lid. Furthermore, the duration of use of the scented insert can be prolonged by the metering unit.

According to a further configuration, the metering unit can be positioned into the receiving unit or into the receiving recess of the lid, above the scented insert, in a rotatable manner. The metering unit can preferably have a round disc form which corresponds to a form of the receiving recess. In this way, the receiving recess can be used, on the circumferential side, as a rotary bearing for the metering unit. Furthermore, the metering unit can be embodied as a closure of the receiving recess, by which closure the scented insert is fastened to the lid in a positionally fixed manner.

The cloths in the receiving space of the housing can be protected from drying out and ingress of dust if the multi-purpose container has a closure for closing the opening. The closure can preferably be embodied as a plug which can close the opening in an air-tight manner. In particular, the closure can be fastenable to the lid in a manner protected against loss via a flexible mount.

According to a further exemplary embodiment, the cloths which can be inserted into the receiving space are designed as wipes. Advantageously, the housing, the lid and/or the closure have a moisture sensor and/or a moisture indicator for indicating a moisture content of the cloths in the receiving space. In this way, the moisture level of the wipes can be indicated. By way of example, a moisture indicator can be realized via a hygrometer or via a chemical indicator, which is arranged in the closure or in the lid.

The intensity of the scented insert can be adjusted in a particularly precise and simple manner if the metering unit has adjustable air slots for producing or for changing the contacting of air with respect to the scented insert. To this end, the metering unit can have two or more portions which can be rotated relative to one another and which, in a closure position, are arranged alongside one another and completely conceal the scented insert. In an open position, the portions can overlap and thus reveal a part of the scented insert.

The receiving space of the housing can be formed in a particularly simple technical manner if the lid can be connected to the housing via a screw connection or a plug-in connection. In addition, unintentional loosening of the lid from the housing can thus be prevented.

According to a further embodiment, the opening is oriented so as to be centred with respect to the receiving space and extends through the lid, the receiving unit, the scented insert and through the metering unit. In this way, all of the components of the multi-purpose container can be configured in a rotationally symmetrical manner and can be oriented concentrically with respect to one another. The opening can run through an axis of rotation of the components of the multi-purpose container, as a result of which the cloths in the receiving space are still accessible in spite of the air freshening function.

A particularly simple handling of the scented insert can be achieved if the metering unit and/or the receiving unit and/or the scented insert can be placed in the receiving recess of the lid in a positionally fixed manner via fastening clips or via a latching connection. It is thus possible to realize a positively locking fastening of the scented insert, directly or by means of the metering unit, in the receiving recess of the lid.

According to a further aspect of the invention, a scented insert is provided, wherein the scented insert can be positioned in a multi-purpose container according to the invention. Preferably, the scented insert can be formed in a circular disc-shaped or flat manner and can have a ring-shaped cross section, which makes unhindered access to the opening of the lid possible.

For this purpose, the scented insert preferably has a removable middle region which can be made to overlap with the opening of the lid and which is connected to an outer ring region via a material weakening. When the scented insert is used in the multi-purpose container, this middle region can be manually separated from the rest of the scented insert in a simple manner by for example being pushed out and in so doing detached in the region of the material weakening. The opening thus also remains freely accessible when the scented insert is used. As an alternative, however, the scented insert can also be used independently of the multi-purpose container. In this case, it is advantageous for the middle region to be left in the scented insert and thus for more material to be available for releasing the scent.

In a preferred development, the scented insert has a tab which is connected to an outer edge of the scented insert via a material weakening. By means of this tab, the scented insert, when used outside of the multi-purpose container, can for example be fastened or hung at a suitable point in a simple manner. For insertion into the receiving unit or receiving recess, this tab can then be manually released from the scented insert in a simple manner and thus no longer prevents the insertion.

In addition, the invention relates to a cartridge which is in particular used for the provision of cloths. The cartridge can be positioned in a receiving space of a multi-purpose container, wherein a multiplicity of cloths can be removed via the opening in the lid of the multi-purpose container. The cartridge can be formed for example in a cylindrical manner and can store cloths. Preferably, the opening can be open on one side. In a state inserted in the housing, the open side of the cartridge is oriented towards the opening of the lid. A cartridge of this kind makes it possible to re-use the multi-purpose container in a particularly simple manner through the use of refill packs or refill cartridges.

The cartridge is preferably configured in the form of an aluminium sleeve which surrounds the cloths which are arranged therein in the form of a roll. This aluminium sleeve thus envelops the cloths and protects them against drying out. In this case, naturally an opening for the removal of the cloths is provided in the aluminium sleeve, wherein this opening can for example be manually torn open prior to use of the cartridge. In this way, the cartridge can be stored for a relatively long period of time, without the cloths drying out.

BRIEF DESCRIPTION OF THE DRAWINGS

Further features, details and advantages of the invention become apparent from the phrasing of the claims and from the following description of the exemplary embodiments with reference to the drawings, in which:

DETAILED DESCRIPTION OF THE INVENTION

Figure 1:
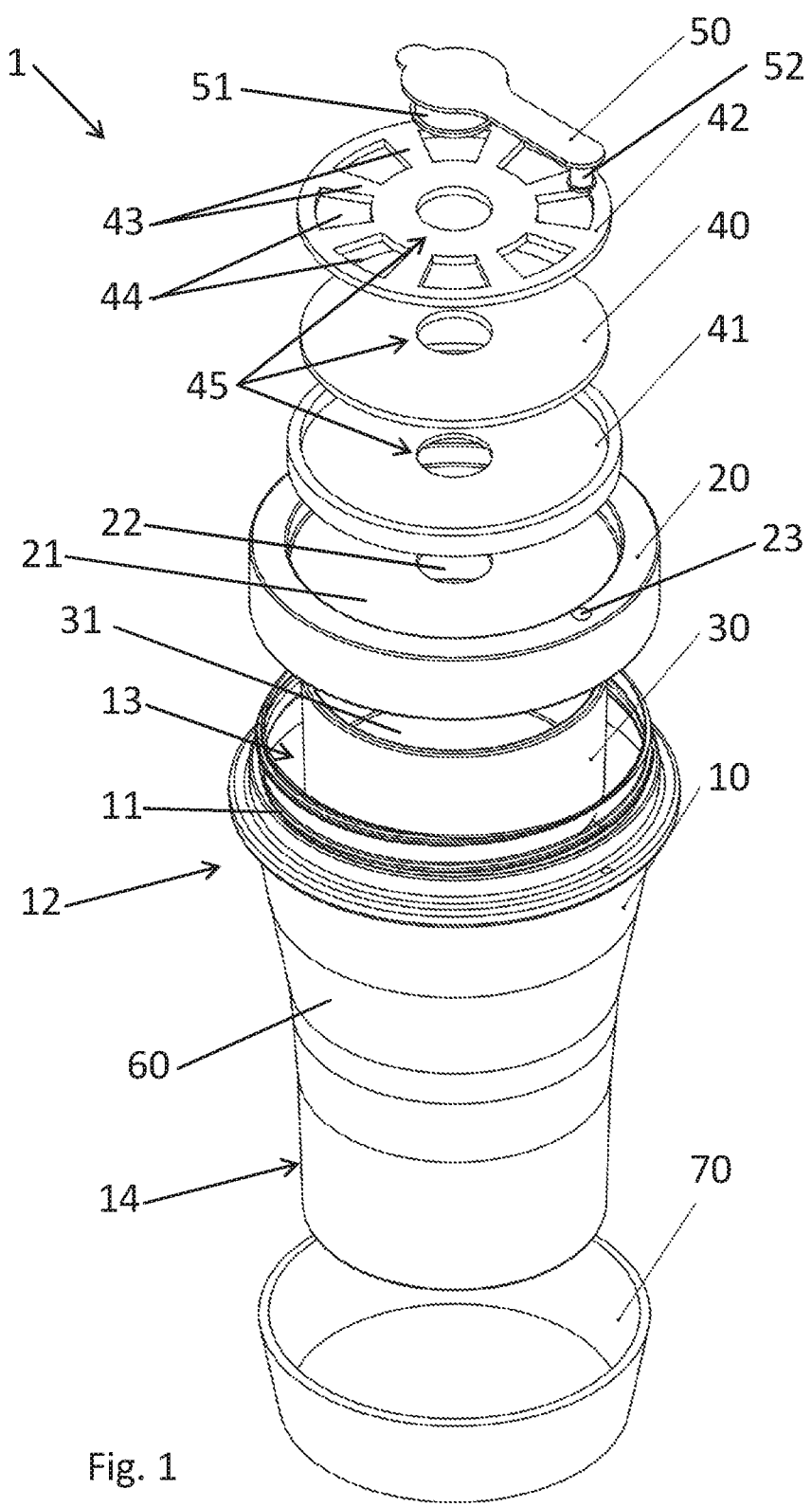
FIG. 1 shows an exploded illustration of a multi-purpose container according to the invention according to one embodiment.

FIG. 1 shows an exploded illustration of a multi-purpose container 1 according to the invention according to one embodiment. The multi-purpose container 1 can preferably be positioned in a drink holder of a passenger car or heavy goods vehicle and can thus provide additional functions.

The multi-purpose container 1 has a housing 10 which is of cup-shaped embodiment. The housing 10 is open on one side and has a thread 11. The thread 11 is arranged on a flared portion 12 of the housing 10. The housing 10 can be produced from plastic, bamboo, wood, glass and the like.

Furthermore, a receiving space 13 can be formed in the housing 10. To this end, the multi-purpose container 1 has a lid 20 which can be screwed to the housing 10 via the thread 11.

The lid 20 is for example composed of a plastic and can close the housing 10 at the end side. The lid 20 has a receiving recess 21. In the installed state of the lid 20, the receiving recess 21 points away from the housing 10. An opening 22 is introduced into the lid 20. The opening 22 is centred or positioned centrally in the lid 20 and produces a connection to the receiving space 13 of the housing 10. In addition, the lid 20 has a bore 23 which is introduced into the lid 20 at the edge side and parallel to the opening 22.

A cartridge 30 can be inserted in the receiving space 13 of the housing 10. The cartridge 30 is formed in a cylindrical manner and is used for the provision of cloths 31, such as, for example, cleaning cloths. To this end, the cartridge 30, analogously to the housing 10, is open at the end side in such a way that the cloths 31 can be removed via the opening 22 of the lid 20.

A scented insert 40 can be inserted into the receiving recess 21. According to the exemplary embodiment, the scented insert 40 can be inserted into the receiving recess 21 by means of a receiving unit 41. The receiving unit 41 is composed of an elastic material, such as, for example, silicone or rubber, and can also receive a metering unit 42 in addition to the scented insert 40. As a result of the elastic material properties, the receiving unit 41 engages circumferentially around the scented insert 40 and the metering unit 42 and produces a positively locking connection. In this way, the metering unit 42, the scented insert 40 and the receiving unit 41 form a contiguous component which can be inserted, as a whole, into the receiving recess 21.

In particular, the metering unit 42 rests on the scented insert 40 and conceals the latter in certain regions. To this end, the metering unit 42 has portions 43 for concealing the scented insert 40, and air slots 44 formed between the portions 43 for exposing the scented insert 40 in certain regions. The multi-purpose container 1 is designed in a substantially rotationally symmetrical manner. The receiving unit 41, the scented insert 40 and the metering unit 42 are therefore also configured in a rotationally symmetrical manner. In this way, the metering unit 42 can be rotated relative to the scented insert 40.

To enable access to the opening 22 of the lid 20, a centred cutout 45 is provided in each case in the scented insert 40, the receiving unit 41 and the metering unit 42 in order to prevent concealment of the opening 22. The centred cutouts 45 are preferably congruent with the opening 22.

If moist cloths 31 are used, an optional closure 50 can be provided. The closure 50 has a bung portion 51 which can be inserted into the opening 22 through the cutouts 45. A retaining portion 52 is connected to the bung portion 51. The retaining portion 52 can be plugged into the bore 23 of the lid 20 in order to prevent unintentional loss of the closure 50. Preferably, the closure 50 can be formed of an elastic material.

For the sale of the multi-purpose container 1, a sticker 60 can additionally be provided, said sticker being able to be attached to a lateral surface 14 of the housing 10. The sticker 60 can for example be used for advertising purposes or as decoration.

At the bottom, an adapter sleeve 70 can be attached to the housing 10, by way of which sleeve the multi-purpose container 1 can be adapted to drink holders with larger diameters. The adapter sleeve 70 is embodied as an elastic cover.

Figure 2:
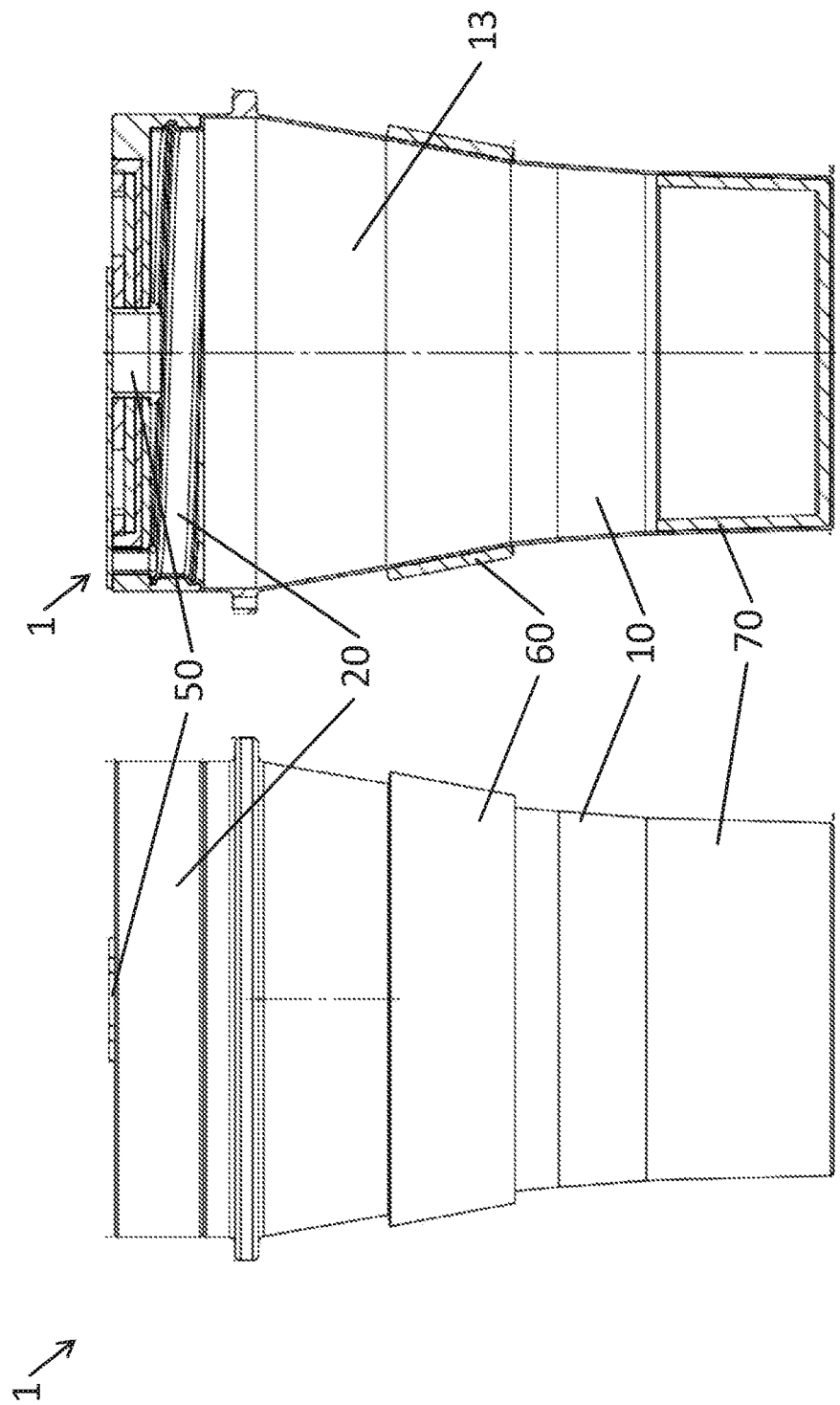
FIG. 2a illustrate a side view of the multi-purpose container of FIG. 1.
FIG. 2b shows a cross sectional view through the multi-purpose container of FIG. 2a in an assembled state.

FIG. 2a and FIG. 2b illustrate side views of the multi-purpose container 1 according to the invention. In particular, FIG. 2b shows a cross section through the multi-purpose container 1, which illustrates the construction of the multi-purpose container 1 in the assembled state.

Here, the closure 50 is inserted into the opening 22 of the lid 20 in order to close the receiving space 13 of the housing 10 in an air-tight manner. For the sake of overview, the cartridge 30 is not illustrated.

Figure 3:
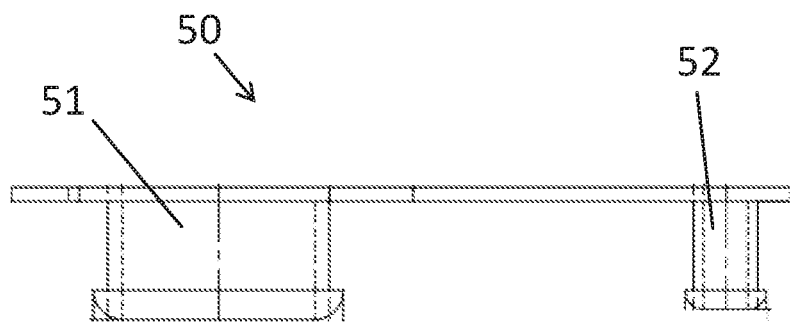
FIG. 3 shows an illustration of a closure for a multi-purpose container according to the invention.

FIG. 3 shows an illustration of a closure 50 for the multi-purpose container 1 according to the invention. In particular, the closure 50 is illustrated in a side view, in which the bung portion 51 and the retaining portion 52, spaced apart from the bung portion 51, of the closure 50 are illustrated.

Figure 4:
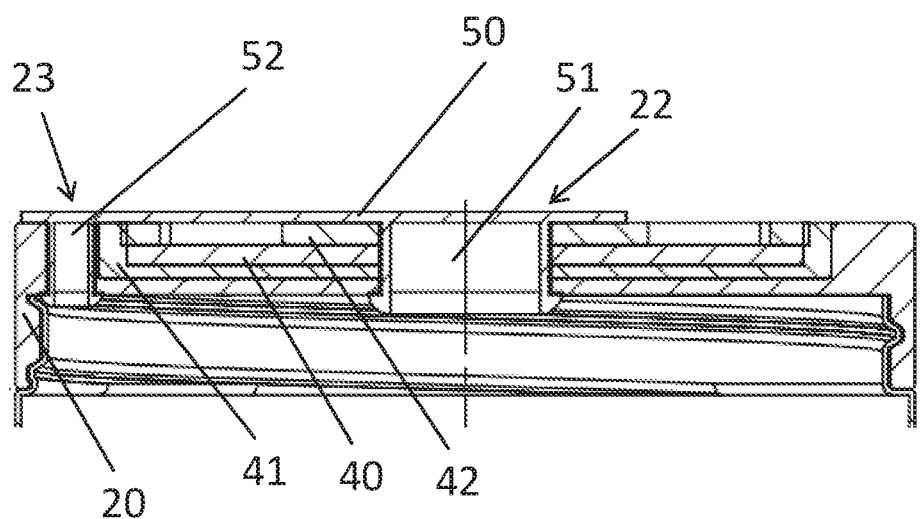
FIG. 4 shows a sectional illustration for illustrating the multi-purpose container according to the invention in the region of a lid.

FIG. 4 shows a sectional illustration for illustrating the multi-purpose container 1 according to the invention in the region of the lid 20. Here, the closure 50 is likewise inserted into the lid 20 in order to close the opening 22. The bung portion 51 of the closure 50 fills the opening 22 in an air-tight manner. The retaining portion 52 is introduced in the edge-side bore 23.

The scented insert 40, the receiving unit 41 and the metering unit 42 are inserted in the receiving recess 21 of the lid 20 and terminate flush with the lid 20.

Figure 5:
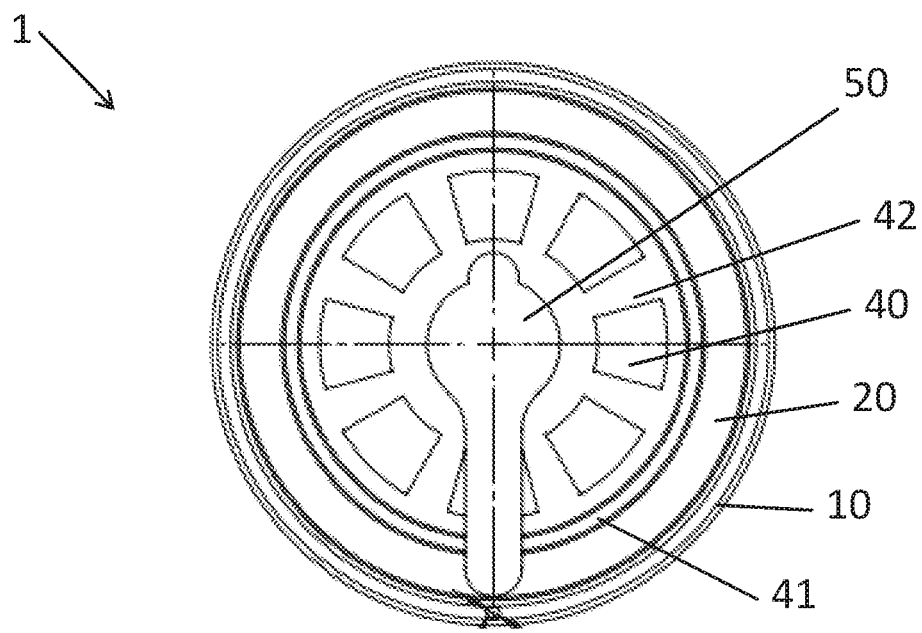
FIG. 5 shows a plan view of the multi-purpose container according to the invention from FIG. 1.
Figure 6:
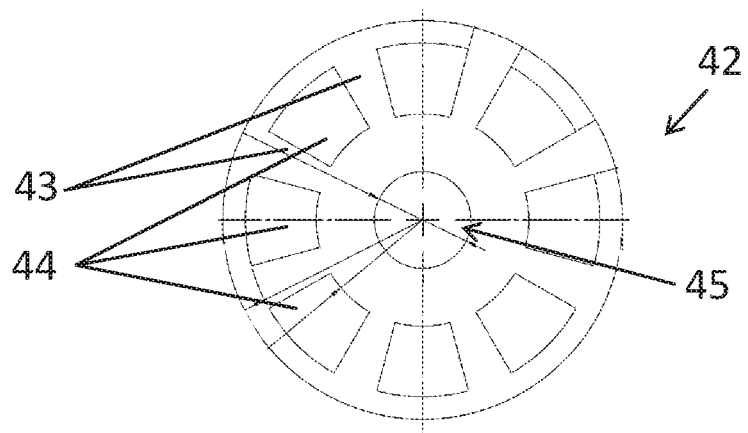
FIG. 6 shows a schematic illustration of a metering device of the multi-purpose container according to the invention and FIG. 7 shows a scented insert.

FIG. 5 illustrates a plan view of the multi-purpose container 1 according to the invention from FIG. 1. The form of the metering unit 42 is in particular illustrated, which is also illustrated separately in FIG. 6. The receiving unit 41 inserted into the receiving recess 21 fills the interspace between the metering unit 42 and the lid 20 in a radial or circumferential manner and thus locks the metering unit 42 in the receiving recess 21 of the lid 20.

Figure 7:
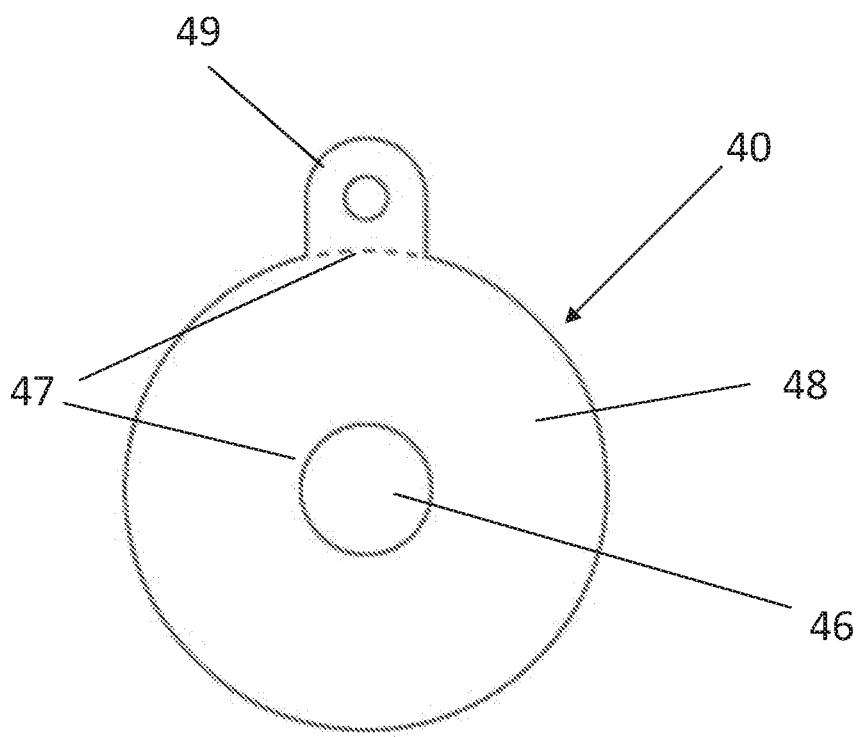

FIG. 7 then shows the scented insert 40 prior to insertion into the receiving unit of the multi-purpose container. The scented insert 40 has a removable middle region 46 which can be made to overlap with the opening 22 of the lid. The middle region 46 is in this case formed centrally within the scented insert 40 and has a circular form. Said middle region is connected to an outer ring region 48 of the scented insert 40 via a material weakening 47. This material weakening 47 is for example embodied as a perforated portion and makes it possible to manually push the middle region 46 out of the scented insert 40 in a simple manner.

The scented insert 40 further has a tab 49 which is likewise connected via a material weakening 47 and which extends in a radial direction. On account of the material weakening 47, the tab 49 can be manually separated from the rest of the scented insert without any problems.

Removal of the middle region 46 and also of the tab 49 makes it possible for the scented insert 40 to be inserted with a precise fit into the receiving unit 41, without then overlapping the opening 22 in the lid 20 of the multi-purpose container 1. Prior to removal of the middle region 46 and of the tab 49, the scented insert can, however, be used independently of the multi-purpose container, wherein the tab 49 makes simple fastening of the scented insert 40 possible, and the middle region 46 provides an additional scent reservoir. The scented insert is thus universally usable.

The invention is not restricted to one of the above-described embodiments, but can be modified in many ways. By way of example, the scented insert 40 can be arrangeable in the receiving recess 21 without a metering unit 42. Furthermore, the form of the multi-purpose container 1 can deviate from the form illustrated, wherein the opening 22 can also be introduced into the lid 20 in an asymmetrical manner. In addition, the scented insert 40 can be embodied in the form of a strip or for example of a ring portion.

Provision can further be made for the multi-purpose container to be equipped with one or more sensors. In this case, these sensors can for example indicate a cloth fill level in a purely optical manner, but also provide information about a moisture content of the cloths or of the scented insert on the basis of a chemical reaction. Here, a sensor of this kind does not need electrical energy.

All of the features and advantages, including structural details, spatial arrangements and method steps, arising from the claims, the description and the drawing may be essential to the invention, both individually and in a wide variety of combinations.

LIST OF REFERENCE DESIGNATIONS

1 Multi-purpose container
10 Housing
11 Thread of the housing
12 Flared portion of the housing
13 Receiving space
14 Lateral surface of the housing
20 Lid
21 Receiving recess
22 Opening
23 Bore
30 Cartridge
31 Cloths
40 Scented insert
41 Receiving unit
42 Metering unit
43 Portions of the metering unit
44 Air slots of the metering unit
45 Centred cutout
46 Middle region
47 Material weakening
48 Outer ring region
49 Tab
50 Closure
51 Bung portion
52 Retaining portion
60 Sticker
70 Adapter sleeve

The invention claimed is:

1. A multi-purpose container (1) with an air freshening function for receiving cloths (31), in particular for use in a drink holder of a vehicle, having a housing (10) and a lid (20) for closing the housing (10) and for forming a receiving space (13) in the housing (10), and having a scented insert (40), wherein the lid (20) has an opening (22) for the removal of cloths (31) from the receiving space (13) and wherein the lid (20) has a receiving recess (21) for receiving the scented insert (40), wherein the scented insert (40) can be inserted into a receiving unit (41), wherein the receiving unit (41), with the scented insert (40) inserted, can be placed in the receiving recess (21) of the lid (20).

2. The multi-purpose container according to claim 1, wherein the receiving space (13) of the housing (10) is configured to receive cloths (31), wherein the cloths (31) can be inserted in a cartridge (30) or directly in the receiving space (13).

3. The multi-purpose moose container according to claim 1, wherein the multi-purpose container (1) has a metering unit (42) which conceals the scented insert (40) at least in certain regions, wherein the metering unit (42) is designed to be displaceable or rotatable relative to the scented insert (40).

4. The multi-purpose container according to claim 1, wherein a metering unit (42) can be positioned into the receiving unit (41) or into the receiving recess (21) of the lid (20), above the scented insert (40), in a rotatable manner.

5. The multi-purpose container according to claim 1, wherein e multi-purpose container (1) has a closure (50) for closing the opening (22).

6. The multi-purpose container according to claim 1, wherein the cloths (31) which can be inserted into the receiving space (13) are designed as wipes, wherein the housing (10), the lid (20) and/or the closure (50) have a moisture sensor and/or a moisture indicator for indicating a moisture content of the cloths (31) in the receiving space (13).

7. The multi-purpose container according to claim 1, wherein the metering unit (42) has adjustable air slots (44) for producing or for changing the contacting of air with respect to the scented insert (40).

8. The multi-purpose container according to claim 1, wherein the lid (20) can be connected to the housing (10) via a screw connection or a plug-in connection.

9. The multi-purpose container according to claim 3, wherein the opening (22) is oriented so as to be centered centered with respect to the receiving space (13) and extends through the lid (20), the receiving unit (41), the scented insert (40) and through the metering unit (42).

10. The multi-purpose container according to claim 1, wherein a metering unit (42) and/or the receiving unit (41) and/or the scented insert (40) can be placed in the receiving recess (21) of the lid (20) in a positionally fixed manner via fastening clips or via a latching connection.

11. A scented insert (40) and multi-purpose container assembly, the multi-purpose container (1) being that according to claim 1, wherein the scented insert (40) is positioned in the multi-purpose container (1).

12. The assembly according to claim 11, characterized in that the scented insert has a removable middle region (46)

which can be made to overlap with the opening (22) of the lid and which is connected to an outer ring region (48) via a material weakening (47).

13. A cartridge and multi-purpose container assembly, the multi-purpose container (1) being that according to claim 1, wherein the cartridge (30) is positioned in the receiving space (13) of the multi-purpose container (1) and wherein cloths (31) can be removed via the opening (22) in the lid (20) of the multi-purpose container (1).

\* \* \* \* \*